US00PP33697P2

(12) United States Plant Patent
van Sambeek

(10) Patent No.: US PP33,697 P2
(45) Date of Patent: Nov. 23, 2021

(54) ***SALVIA* PLANT NAMED 'DOSALMIRO'**

(50) Latin Name: *Salvia nemorosa*
Varietal Denomination: Dosalmiro

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/139,956

(22) Filed: Dec. 31, 2020

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Salvia* plant named 'Dosalmiro', characterized by its compact and upright plant habit; vigorous growth habit; freely branching habit; very dark purple-colored stems; early and freely flowering habit; upright inflorescences with deep purplish pink-colored flowers positioned on very dark purple-colored peduncles; and good garden performance.

1 Drawing Sheet

Botanical designation: *Salvia nemorosa.*
Cultivar denomination: 'DOSALMIRO'.

CROSS-REFERENCED TO CLOSELY-RELATED APPLICATIONS

Title: *Salvia* Plant Named 'DOSALMIPU'
Inventor: Ellen van Sambeek
Filed: Concurrently with this application

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 24, 2020, application number 2020/1986. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Salvia* plant, botanically known as *Salvia nemorosa* and hereinafter referred to by the name 'Dosalmiro'.

The new *Salvia* plant is a product of a planned breeding program conducted by the Inventor in Aalsmeer, The Netherlands. The objective of the breeding program is to create new compact *Salvia* plants with numerous attractive flowers.

The new *Salvia* plant originated from a cross-pollination in April, 2015 of a proprietary selection of *Salvia nemorosa* identified as code number SV13-000096-006, not patented, as the female, or seed, parent with a proprietary selection of *Salvia nemorosa* identified as code number SV13-000314-001, not patented, as the male, or pollen, parent. The new *Salvia* plant was discovered and selected by the Inventor as a single flowering plant from within the progeny of the stated cross-pollination in a controlled environment in Aalsmeer, The Netherlands in April, 2016.

Asexual reproduction of the new cultivar by vegetative terminal cuttings in Aalsmeer, The Netherlands, since June, 2016 has shown that the unique features of this new *Salvia* plant are stable and reproduced true to type in successive generations.

SUMMARY OF THE INVENTION

Plants of the new *Salvia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dosalmiro'. These characteristics in combination distinguish 'Dosalmiro' as a new and distinct *Salvia* plant:

1. Compact and upright plant habit.
2. Vigorous growth habit.
3. Freely branching habit.
4. Very dark purple-colored stems.
5. Early and freely flowering habit.

6. Upright inflorescences with deep purplish pink-colored flowers positioned on very dark purple-colored peduncles.
7. Good garden performance.

Plants of the new *Salvia* can be compared to plants of the parent selections. Plants of the new *Salvia* differ primarily from plants of the parent selections in plant habit as plants of new *Salvia* are more compact and more uniform than plants of the parent selections. In addition, plants of the new *Salvia* have deep purplish pink-colored flowers whereas flowers of plants of the parent selections are purple in color.

Plants of the new *Salvia* can be compared to plants of *Salvia nemarosa* 'Dosalmipu', disclosed in a U.S. Plant Patent application filed concurrently. Plants of the new *Salvia* differ primarily from plants of 'Dosalmipu' in flower color as plants of the new *Salvia* have deep purplish pink-colored flowers whereas flowers of plants of 'Dosalmipu' are dark violet blue in color.

Plants of the new *Salvia* can be compared to plants of *Salvia nemorosa* 'Blue Marvel', disclosed in U.S. Plant Pat. No. 27,018. In side-by-side comparisons, plants of the new *Salvia* differ primarily from plants of 'Blue Marvel' in the following characteristics:

1. Plants of the new *Salvia* have smaller flowers than plants of 'Blue Marvel'.
2. Peduncles of plants of the new *Salvia* are very dark purple in color whereas peduncles of plants of 'Blue Marvel' are yellow green overlain with dark red in color.
3. Flowers of plants of the new *Salvia* are deep purplish pink in color whereas flowers of plants of 'Marvel Blue' are dark violet in color.

BRIEF DESCRIPTION OF THE PHOTOGRAPH

The accompanying colored photograph illustrates the overall appearance of the new *Salvia* plant showing the colors as true as it is reasonably possible to obtain in colored reproductions of this type. Colors in the photograph may differ slightly from the color values cited in the detailed botanical description which accurately describe the actual colors of the new *Salvia* plant.

The photograph is a side perspective view of a typical flowering plant of 'Dosalmiro' grown in a container.

DETAILED BOTANICAL DESCRIPTION

The aforementioned photograph and following observations and measurements describe plants grown in 17-cm containers in Aalsmeer, The Netherlands during the early summer initially in a greenhouse and finished in an outdoor nursery and under conditions and cultural practices which approximate those generally used in commercial *Salvia* plant production. During the production of the plants, day temperatures averaged 21° C. and night temperatures averaged 15° C. Plants were 19 weeks old when the photographs and description were taken. In the following description, color references are made to The Royal Horticultural Society Colour Chart, Second Edition, except where general terms of ordinary dictionary significance are used. Measurements represent averages for typical flowering plants.

Botanical classification: *Salvia nemorosa* 'Dosalmiro'.

Parentage:

*Female, or seed, parent*.—Proprietary selection of *Salvia nemorosa* identified as code number SV13-000096-006, not patented.

*Male, or pollen, parent*.—Proprietary selection of *Salvia nemorosa* identified as code number SV13-000314-001, not patented.

Propagation:

*Type*.—By vegetative terminal cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; compact and upright plant habit; uniform and vigorous growth habit; and moderate growth rate.

*Branching habit*.—Freely basal branching with about six primary lateral branches each with about eight secondary lateral branches developing per plant.

*Plant height*.—About 29 cm.

*Plant width*.—About 23 cm.

*Lateral branch description*.—Length: About 15 cm. Internode length: About 4 cm. Strength: Strong. Aspect: Erect to about 15° from vertical. Texture and luster: Slightly pubescent; glossy. Color: Close to 144A heavily overlain with close to 202A.

Leaf description:

*Arrangement*.—Opposite and decussate; simple.

*Length*.—About 6 cm.

*Width*.—About 2.5 cm.

*Shape*.—Elliptical.

*Apex*.—Acuminate.

*Base*.—Cordate.

*Margin*.—Crenate with shallow divergent lobes.

*Texture and luster, upper and lower surfaces*.—Smooth, glabrous; lamina, matte and venation, glossy.

*Venation pattern*.—Pinnate, reticulate.

*Color*.—Developing leaves, upper surface: Close to 137A. Developing leaves, lower surface: Close to 137C. Fully expanded leaves, upper surface: Close to 147A; venation, close to 147C. Fully expanded leaves, lower surface: Close to 147A; venation, close to 147D.

*Petioles*.—Length: About 1 cm. Diameter: About 3 mm. Strength: Moderately strong. Texture and luster, upper and lower surfaces: Smooth, glabrous; glossy. Color, upper surface: Close to 147C. Color, lower surface: Close to 147D.

Flower description:

*Flower arrangement and shape*.—Single bilabiate flowers arranged on erect spikes; freely flowering habit with about 40 flowers developing per inflorescence and about 3,772 flowers developing per plant during the flowering season; flowers face mostly outwardly; flowers sessile.

*Fragrance*.—Slightly fragrant, pleasant.

*Natural flowering season*.—Early flowering habit, plants begin flowering about nine weeks after planting; plants flower during the month of June in an outdoor environment in The Netherlands; flowers not persistent.

*Flower buds*.—Length: About 6 mm. Diameter: About 3 mm. Shape: Elliptical. Texture and luster: Smooth, glabrous; matte. Color: Close to 74A.

*Inflorescence height*.—About 14.5 cm.

*Inflorescence diameter*.—About 2 cm.

*Flower size*.—About 4 mm by 9 mm.

*Flower depth*.—About 1 cm.

*Flower throat diameter*.—About 1 mm.

*Flower tube length*.—About 2 mm.

*Flower tube diameter, proximally*.—About 1 mm.

*Petals*.—Arrangement: Five petals fused at the base; one upper banner petal (upper lip), two lateral petals and two lower petals (lower lip). Lobe length: About 5 mm. Lobe width: About 5 mm. Lobe shape: Roughly spatulate. Apex: Round. Base: Fused into a narrow tube. Margin: Entire. Texture and luster, upper and lower surfaces: Smooth, glabrous; matte. Texture and luster, throat: Smooth, glabrous; matte. Texture and luster, tube: Smooth, glabrous; matte. Color: When opening, upper and lower surfaces: Close to 68A. Fully opened, upper and lower surfaces: Close to 68A; venation, close to 68A; color does not change with development. Throat: Close to 68A; venation, close to 68A. Tube: Close to 155D; venation, close to 155D.

*Calyx*.—Arrangement: About four or five sepals fused to form a campanulate calyx. Length: About 6 mm. Width: About 2 mm. Shape: Deltoid, subulate. Apex: Acuminate. Margin: Entire. Texture and luster, inner and outer surfaces: Smooth, glabrous; semi-glossy. Color, inner surface: Close to 187A. Color, outer surface: Close to 146A.

*Flower bracts*.—Quantity: One per flower. Length: About 9 mm. Width: About 5 mm. Shape: Roughly ovate with acuminate apex. Texture and luster, upper and lower surfaces: Smooth, glabrous; semi-glossy. Color: Close to 187A and 186A.

*Peduncles*.—Length: About 14.5 cm. Diameter: About 2 mm. Strength: Moderately strong. Aspect: Erect to about 25° from vertical. Texture and luster: Slightly pubescent; glossy. Color: Close to 202A.

*Reproductive organs*.—Stamens: Quantity per flower: Two. Filament length: About 2 mm. Filament color: Close to 68D. Anther shape: Oblique. Anther size: About 1 mm by 0.5 mm. Anther color: Close to 164A. Pollen amount: None observed. Pistils: Quantity per flower: One. Pistil length: About 1 cm. Stigma diameter: About 1 mm. Stigma shape: Biparted. Stigma color: Close to 72A. Style length: About 9 mm. Style color: Close to 155D. Ovary color: Close to 143A.

*Seeds and fruits*.—To date, seed and fruit production has not been observed on plants of the new *Salvia*.

Pathogen & pest resistance: To date, plants of the new *Salvia* have not been noted to be resistant to pathogens and pests common to *Salvia* plants.

Garden performance: Plants of the new *Salvia* have exhibited good tolerance to rain, wind and to tolerate temperatures ranging from −35° C. to about 35° C. and to be suitable for USDA Hardiness Zone 3.

It is claimed:

1. A new and distinct *Salvia* plant named 'Dosalmiro' as illustrated and described.

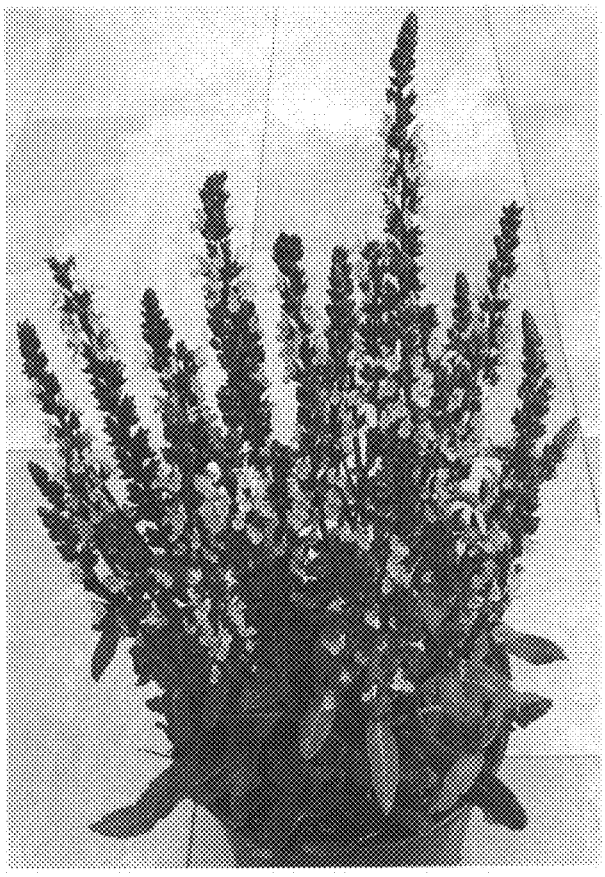

* * * * *